United States Patent
Bonelli

(10) Patent No.: US 12,145,301 B2
(45) Date of Patent: Nov. 19, 2024

(54) ELASTIC FILM, A METHOD FOR PRODUCING AN ELASTIC FILM, AND A METHOD FOR PRODUCING ELASTIC LAMINATES

(71) Applicant: Fameccanica.Data S.p.A., San Giovanni Teatino (IT)

(72) Inventor: Guido Bonelli, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 0 days.

(21) Appl. No.: 17/861,541

(22) Filed: Jul. 11, 2022

(65) Prior Publication Data

US 2023/0009362 A1    Jan. 12, 2023

(30) Foreign Application Priority Data

Jul. 12, 2021   (EP) ..................... 21184968

(51) Int. Cl.
- *B29C 48/21* (2019.01)
- *B29C 48/00* (2019.01)
- *B29C 48/08* (2019.01)

(52) U.S. Cl.
CPC .......... *B29C 48/21* (2019.02); *B29C 48/0018* (2019.02); *B29C 48/0021* (2019.02); *B29C 48/0022* (2019.02); *B29C 48/08* (2019.02)

(58) Field of Classification Search
CPC ............. G06Q 20/227; G06Q 20/3226; G06Q 20/326; G06Q 20/36; G06Q 20/3674; A61F 13/15699; A61F 13/15723; A61F 13/4902; A61F 2013/49025; A61F 2013/49031; B29C 2793/0063; B29C 48/0018; B29C 48/0021; B29C 48/0022; B29C 48/08; B29C 48/21; B32B 2307/51; B32B 2555/02; B32B 27/08; B32B 27/32; B32B 3/085; B32B 5/266
See application file for complete search history.

(56) References Cited

FOREIGN PATENT DOCUMENTS

| EP | 0548609 A1 | 6/1993 |
| EP | 3092997 A1 | 11/2016 |
| WO | 2005065932 A1 | 7/2005 |
| WO | 2009025975 A1 | 2/2009 |
| WO | WO 2020230012 | * 11/2020 | ............. A61F 13/15 |

OTHER PUBLICATIONS

Benjamin, CN 110058364 A (Year: 2019).*
European Search Report dated Jan. 19, 2022. 7 pages.

* cited by examiner

*Primary Examiner* — Lawrence D Ferguson
(74) *Attorney, Agent, or Firm* — RMCK Law Group PLC

(57) ABSTRACT

An elastic film including a plurality of parallel elastic ribbons elongated in a longitudinal direction and spaced apart from each other in a transverse direction orthogonal to the longitudinal direction, wherein the elastic ribbons are coated on at least one surface by at least one skin layer which joins the plurality of parallel elastic ribbons to each other.

8 Claims, 4 Drawing Sheets

ELASTIC FILM, A METHOD FOR PRODUCING AN ELASTIC FILM, AND A METHOD FOR PRODUCING ELASTIC LAMINATES

CROSS-REFERENCE TO RELATED APPLICATION

This application claims priority to European Patent Application No. 21184968.2 filed Jul. 12, 2021. The disclosure of the above application is incorporated herein by reference in its entirety.

FIELD OF THE INVENTION

The present invention relates to an elastic film.

The invention has been developed in particular in view of its application in the field of absorbent sanitary articles, such as, for example, diapers, training pants, absorbent sanitary products for incontinent adults, etc.

The present invention also relates to a method for producing an elastic film and to a method for producing elastic laminates, in particular for absorbent sanitary articles.

PRIOR ART

An absorbent sanitary article typically includes several elastic elements, such as elastic waist bands, elastic leg cuffs, elastic side panels, etc.

A traditional method for manufacturing elastic elements for absorbent sanitary articles consists in providing a plurality of elastic wires which are unwound from respective reels and supplied parallel to each other and longitudinally stretched in a machine direction. The plurality of parallel elastic wires is enclosed and fixed between two non-woven webs. Fixing the elastic wires between the non-woven webs may be carried out by glue or by a pattern of spot welds, e.g. as disclosed in EP3092997. A problem of this method it the high complexity of the devices for unwinding and feeding a very high number of elastic wires with controlled longitudinal tension. In case of break of one of the elastic wires the whole line for manufacturing absorbent sanitary article has to be stopped to replace or repair the broken wire.

Another method for manufacturing elastic elements for absorbent sanitary articles consists in providing a continuous elastic film unwound from a reel and stretched in a longitudinal o in transverse direction, which is enclosed between two webs of non-woven material and is fixed thereto by a pattern of glue spots or spot welds. One of the drawbacks of this method is that there are problems when the width of the elastic film is small. Reels of continuous elastic films should have a minimum width of 50 mm in order to ensure stability of the reel. Elastic films having a width lower than 50 mm should be wound in spool rolls, which complicate the unwinding devices.

US2003/30017345 A1 discloses an elastic film having activated and non-activated zones formed during an activation process. The activated zones allow the film to expand without generating excessive tensional forces. The film has M-polypropylene or M-polyethlyene skin layers and a core layer having an elastomeric polyurethane, ethylene copolymer such as ethylene vinyl acetate, an ethylene/propylene copolymer elastomer or ethylene/propylene/diene terpolymer elastomer. The activation process allows the skin layers to behave more like the core layer.

DE102015114985 A1 discloses a method for producing a film with areas of different elastic extensibility, wherein a coextruded film with an elastic film layer and at least one non-elastic film layer is provided, wherein the non-elastic film layer is at least partially destroyed by a laser radiation.

EP0521883 A1 discloses microtextured elastomeric laminates comprising at least one elastomeric layer and at least one thin skin layer, prepared by coextrusion of the layers followed by stretching the laminate past the elastic limit of the skin layers in predetermined regions of the laminate and then allowing the laminate to recover in these regions.

OBJECT AND SUMMARY OF THE INVENTION

The object of the present invention is to overcome the problems of the prior art.

According to the invention, this object is achieved by an elastic film according to claim 1.

According to other aspects, the invention relates to a method for producing an elastic laminate having the features of claim 9 and to a method for producing an elastic film having the features of claim 13 or 14.

The claims form an integral part of the technical disclosure provided here in relation to the invention.

BRIEF DESCRIPTION OF THE DRAWINGS

The present invention will now be described with reference to the attached drawings, provided purely by way of non-limiting example, wherein.

It should be appreciated that the attached drawings are schematic and not to scale with respect to real products. Various figures may not be represented in the same scale. Also, in various figures some elements may not be shown to better show other elements.

DETAILED DESCRIPTION

Figure 2:
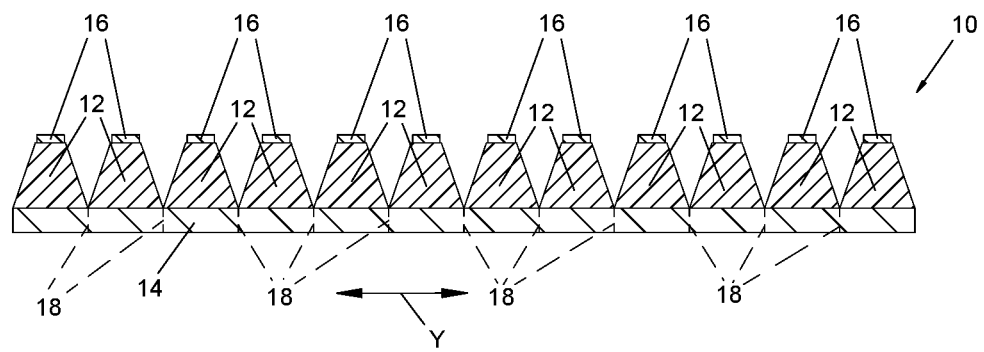
FIG. 2 is a schematic cross-section showing a first embodiment of an elastic film according to the present invention obtained by cutting longitudinally the extruded elastic film of FIG. 1.

With reference to FIG. 2, an elastic film according to a first embodiment of the present invention is indicated by the reference number 10.

The elastic film 10 comprises a plurality of parallel elastic ribbons 12 elongated in a longitudinal direction and spaced apart from each other in a transverse direction Y orthogonal to the longitudinal direction.

The elastic ribbons 12 are coated on two opposite surfaces by first and second skin layers 14, 16. The first skin layer 14 is continuous in the transverse direction Y and joins the elastic ribbons 12 to each other. The second skin layer 16 is discontinuous in the transverse direction Y and coats the surfaces of the elastic ribbons 12 opposite to the first skin layer 14.

The first skin layer 14 may have a plurality of parallel longitudinal break lines 18, each of which extends between each pair of adjacent elastic ribbons 12.

Figure 1:
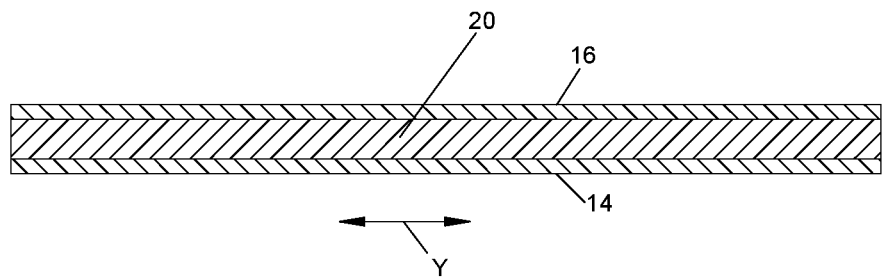
FIG. 1 is a schematic cross section of an extruded elastic film.

With reference to FIG. 1, the elastic film 10 of FIG. 2 may be produced by extruding a transversely continuous flat elastic element 20 of elastic material and applying first and second transverse continuous skin layers 14, 16 on opposite surfaces of the transversely continuous flat elastic element 20. The first and second transversely continuous skin layers 14, 16 may be co-extruded with the transversely continuous flat elastic element 20.

Then, the transversely continuous flat elastic element 20 and the second skin layer 16 are cut longitudinally, e.g. by rotating knives, so as to divide the continuous elastic core 20 in a plurality of parallel elastic ribbons 12. The longitudinal break lines 18 on the first skin layer 14 may be formed simultaneously with the longitudinal cuts that form the parallel elastic ribbons 12.

Figure 3:
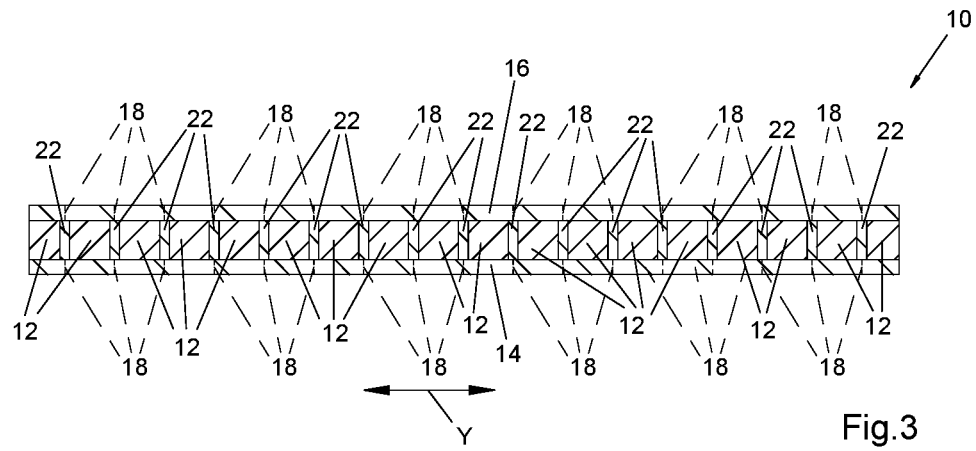
FIG. 3 is a schematic cross-section showing a second embodiment of an elastic film according to the present invention.

With reference to FIG. 3, in a second embodiment of the present invention the elastic film 10 comprises a plurality of parallel elastic ribbons 12 elongated in a longitudinal direction and spaced apart from each other in a transverse direction Y orthogonal to the longitudinal direction. The elastic ribbons 12 are coated on two opposite surfaces by first and second skin layers 14, 16 which are both continuous in the transverse direction Y and both join the elastic ribbons 12 to each other.

In a possible embodiment, the spacing in the transverse direction Y between the parallel elastic ribbons 12 may be variable.

In a possible embodiment, at least two parallel elastic ribbons 12 may be different from each other e.g. they may be made of different materials and/or they may have different shapes.

The elastic film 10 of FIG. 3 may be produced by extruding a plurality of separate parallel elastic ribbons 12 of elastic material and applying first and second transversely continuous skin layers 14, 16 on opposite surfaces of the parallel elastic ribbons 12. The first and second transversely continuous skin layers 14, 16 may be co-extruded with the parallel elastic ribbons 12.

Longitudinal spacers elements 22 of non-elastic filling material, e.g. wax, may be provided between each pair of adjacent elastic ribbons 12. The longitudinal spacers elements 22 may be co-extruded together with the separate parallel elastic ribbons 12 and the first and second transversely continuous skin layers 14, 16.

In the embodiment of FIG. 3 both the first and the second skin layers 14, 16 may have a plurality of parallel longitudinal break lines 18, formed for instance by cutting knives, each of which extends between each pair of adjacent elastic ribbons 12.

The elastic ribbons 12 may be made of a material selected among: styrene block copolymer, elastic polyolefin, thermoplastic urethane. The elastic ribbons may have an elastic elongation comprised between 200 and 400%.

The skin layers 14, 16 may be made of a material selected among: low density polyethylene (LDPE), low density polypropylene (LDPP), and elastic polyolefin added with thermoplastic materials.

Figure 9:
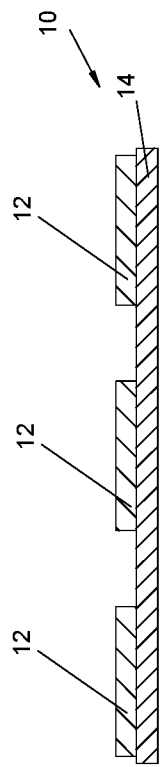
FIGS. 9-13 are schematic cross-sections showing possible embodiments of elastic films according to the present invention.

In the embodiment of FIG. 9 the parallel elastic ribbons 12 may be coated on only one surface by only one skin layer 14 continuous in the transverse direction Y, which joins the parallel elastic ribbons 12 to each other. The embodiment of FIG. 9 is cheap but may be difficult to handle because the uncoated surfaces of the elastic ribbons 12 may be sticky.

In the embodiment of FIGS. 10-13 the parallel elastic ribbons 12 are coated on two opposite surfaces by first and second skin layers 14, 16, so as to increase the stability and to facilitate wounding of the film 10 in reels.

Figure 10:
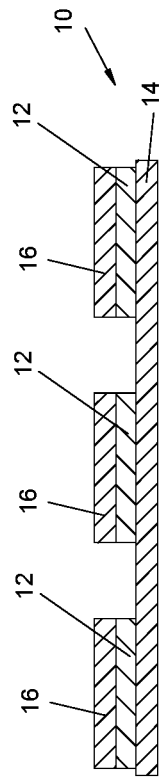

In the embodiment of FIG. 10 the first skin layer 14 is continuous in the transverse direction Y and joins the elastic ribbons 12 to each other, and the second skin layer 16 is discontinuous in the transverse direction Y and coats the surfaces of the elastic ribbons 12 opposite to the first skin layer 14.

Figure 11:
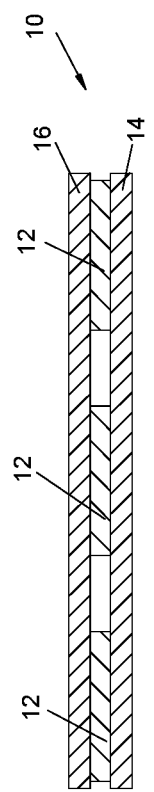

In the embodiment of FIG. 11 the first and second skin layers 14, 16 are both continuous in the transverse direction and both join the elastic ribbons 12 to each other, and empty spaces may extend between the elastic ribbons 12.

Figure 12:
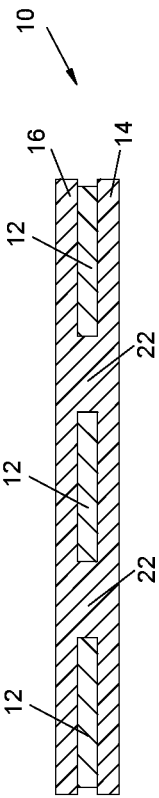

In the embodiment of FIG. 12 non-elastic filling elements 22, which may be integrally formed with the skin layers 14, 16, may fill the spaces between each pair of adjacent elastic ribbons 12.

Figure 13:
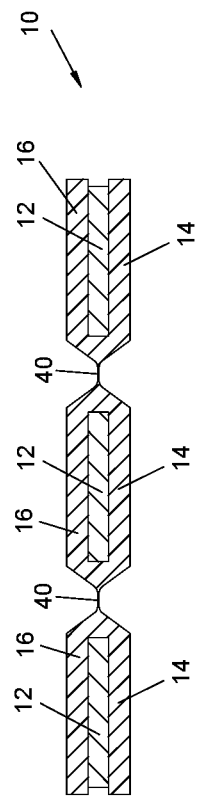

In the embodiment of FIG. 13 in the spaces between each pair of adjacent elastic ribbons 12 the first and second skin layers 14, 16 may be calendered by a ring roller so as to form weakened portions 40 in the spaces between the adjacent elastic ribbons 12. In a possible embodiment the weakened portions 40 may be coextruded with the skin layers 14, 16.

The elastic film 10 may be used for producing an elastic laminate, in particular in machines for manufacturing absorbent sanitary articles.

The elastic film 10 with an indefinite extension in the longitudinal direction is wound in a reel, which is arranged in an unwinding device which unwinds the elastic film 10 from the reel and feeds the elastic film 10 in a machine direction parallel to the longitudinal extension of the elastic film 10.

In a first step the elastic ribbons 12 are detached from each other.

In a possible embodiment, detaching from each other the elastic ribbons 12 may be carried out by breaking the longitudinal portions of the at least one skin layer 14, 16 which join to each other the parallel elastic ribbons 12.

Figure 4:
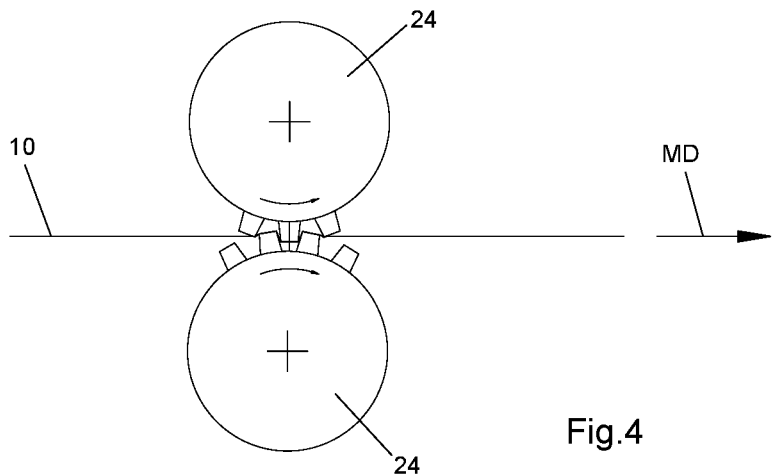
FIGS. 4, 5 and 6 are schematic side views showing different methods for detaching from each other parallel elastic ribbons of the elastic films of FIGS. 1 and 2.

With reference to FIG. 4, breaking the longitudinal portions of the at least one skin layer 14, 16 which join to each other the parallel elastic ribbons 12 may be carried out by passing the elastic film 10 between two mutually meshing toothed wheels 24. During the passage of the elastic film 10 between the mutually meshing toothed wheels 24 the elastic ribbons 12 are stretched longitudinally. The longitudinal extension of the elastic ribbons 12 generates a transverse compression thereof, which breaks the longitudinal portions of the at least one skin layer 14, 16 which join to each other the parallel elastic ribbons 12. Breaking the longitudinal portions of the at least one skin layer 14, 16 may be facilitated by the longitudinal break lines 18.

Figure 5:
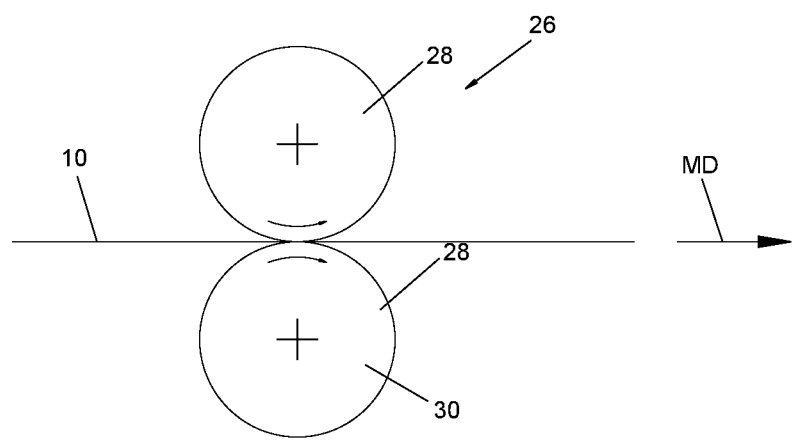

With reference to FIG. 5, in another possible embodiment, detaching from each other the elastic ribbons 12 may be carried out by cutting the longitudinal portions of the at least one skin layer 14, 16 which join to each other the parallel elastic ribbons 12, e.g. by a longitudinal cutting device 26 comprising a plurality of parallel cutting disks 28 cooperating with an anvil roller 30.

Figure 6:
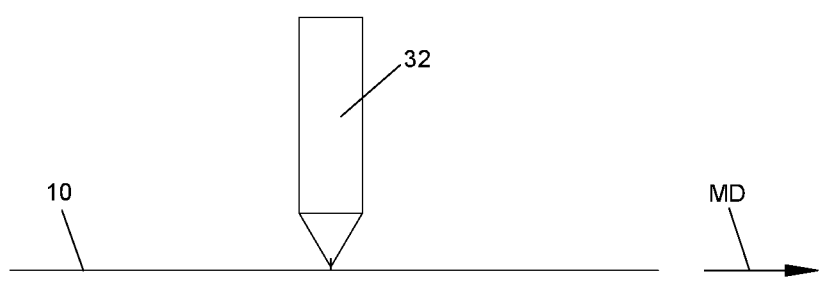

With reference to FIG. 6, in another possible embodiment, detaching from each other the elastic ribbons 12 may be carried out by fusing, e.g. by a plurality of laser nozzles 32 the longitudinal portions of the at least one skin layer 14, 16 which join to each other the parallel elastic ribbons 12.

After detaching from each other the elastic ribbons 12, the elastic film 12 is converted into a plurality of separate elastic ribbons 12 which move in a machine direction MD parallel to the longitudinal axes of the elastic ribbons 12.

Figure 7:
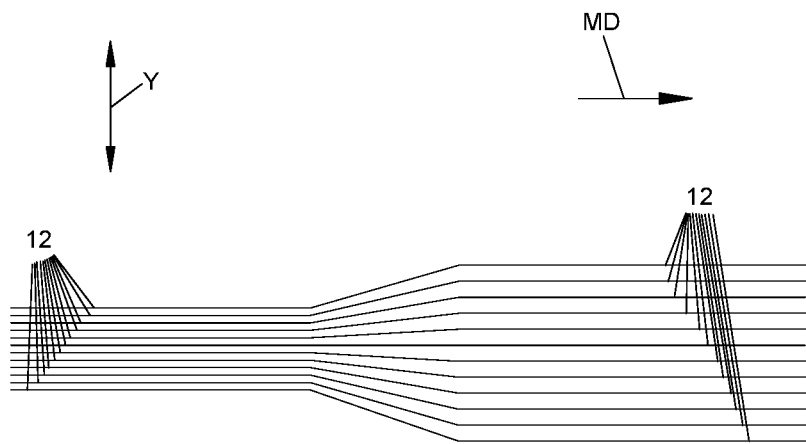
FIG. 7 is a schematic plan view showing a step for producing an elastic laminate.

With reference to FIG. 7, the separate elastic ribbons 12 are then spaced from each other in the transverse direction Y as the move in the machine direction MD.

Figure 8:
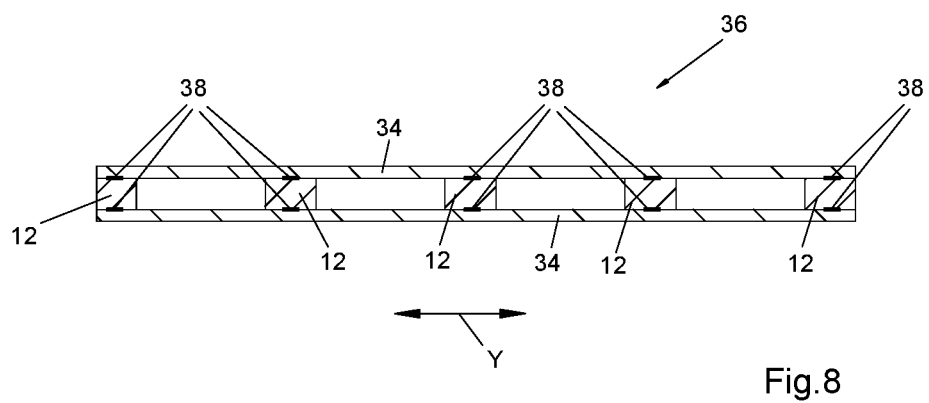
FIG. 8 is a schematic cross-section showing an elastic laminate according to the present invention.

The spaced apart elastic ribbons 12 are stretched in the machine direction MD, either before or after spacing the elastic ribbons 12 from each other in the transverse direction Y. As shown in FIG. 8, the elastic ribbons 12 are enclosed between two opposite non-woven webs 34, while longitudinally stretched in the machine direction MD. The elastic ribbons 12 longitudinally stretched in the machine direction MD are fixed to the two opposite non-woven webs 34 to form a continuous elastic laminate 36.

The elastic ribbons 12 may be fixed to the two opposite non-woven webs 34 by a pattern of glue spots or spot welds 38. In a possible embodiment the longitudinally tensioned elastic ribbons 12 are fixed in discrete points to the two non-woven webs 34 by welds forming mechanical anchoring points, as disclosed in EP3092997 and U.S. Pat. No. 6,291,039.

An elastic film 10 according to the present invention has considerable advantages in machines for manufacturing absorbent sanitary articles. As compared to machines where the elastic laminates are formed starting from many elastic wires unwound from respective reels, the elastic film according to the present invention requires only one unwinding device, instead of the large number of unwinding devices associated to the respective wires. As compared to elastic laminates produced starting from elastic films, the present invention has no limitations on the width of the elastic laminates and provides elastic laminates which have a far greater permeability to air (breathability) than elastic laminates produced using elastic films of the prior art.

Of course, without prejudice to the principle of the invention, the details of construction and the embodiments can be varied, even significantly, with respect to those illustrated here without departing from the scope of the invention as defined by the following claims.

The invention claimed is:

1. An elastic film, comprising:
a plurality of parallel elastic ribbons elongated in a longitudinal direction and spaced apart from each other in a transverse direction orthogonal to said longitudinal direction,
wherein said plurality of parallel elastic ribbons are coated on at least one surface by at least one skin layer continuous in said transverse direction which joins said plurality of parallel elastic ribbons to each other,
wherein said plurality of parallel elastic ribbons are coated on two opposite surfaces by first and second skin layers, and
wherein said first skin layer is continuous in said transverse direction and joins said plurality of parallel elastic ribbons to each other, and wherein the second skin layer is discontinuous in said transverse direction and coats surfaces of said plurality of parallel elastic ribbons opposite to said first skin layer.

2. An elastic film, comprising:
a plurality of parallel elastic ribbons elongated in a longitudinal direction and spaced apart from each other in a transverse direction orthogonal to said longitudinal direction,
wherein said plurality of parallel elastic ribbons are coated on at least one surface by at least one skin layer continuous in said transverse direction which joins said plurality of parallel elastic ribbons to each other,
wherein said plurality of parallel elastic ribbons are coated on two opposite surfaces by first and second skin layers, and
wherein said first and second skin layers are both continuous in said transverse direction and both join said plurality of parallel elastic ribbons to each other.

3. An elastic film, comprising:
a plurality of parallel elastic ribbons elongated in a longitudinal direction and spaced apart from each other in a transverse direction orthogonal to said longitudinal direction,
wherein said plurality of parallel elastic ribbons are coated on at least one surface by at least one skin layer continuous in said transverse direction which joins said plurality of parallel elastic ribbons to each other, and
a plurality of non-elastic filling elements extending between pairs of adjacent elastic ribbons of the plurality of parallel elastic ribbons.

4. An elastic film, comprising:
a plurality of parallel elastic ribbons elongated in a longitudinal direction and spaced apart from each other in a transverse direction orthogonal to said longitudinal direction,
wherein said plurality of parallel elastic ribbons are coated on at least one surface by at least one skin layer continuous in said transverse direction which joins said plurality of parallel elastic ribbons to each other, and
wherein the at least one skin layer comprises first and second skin layers, and wherein at least one of said first and second skin layers has a plurality of parallel longitudinal break lines each of which extends between pairs of adjacent elastic ribbons of the plurality of parallel elastic ribbons.

5. An elastic film, comprising:
a plurality of parallel elastic ribbons elongated in a longitudinal direction and spaced apart from each other in a transverse direction orthogonal to said longitudinal direction,
wherein said plurality of parallel elastic ribbons are coated on at least one surface by at least one skin layer continuous in said transverse direction which joins said plurality of parallel elastic ribbons to each other, and
at least two parallel elastic ribbons of the plurality of parallel elastic ribbons that are different from each other.

6. The elastic film of claim 1, wherein the spacing in said transverse direction between said plurality of parallel elastic ribbons is variable.

7. The elastic film of claim 1, wherein said plurality of parallel elastic ribbons are made of a material selected among: styrene block copolymer, elastic polyolefin, and thermoplastic urethane.

8. The elastic film of claim 1, wherein said at least one skin layer is made of a material selected among: low density polyethylene (LDPE), low density polypropylene (LDPP), and elastic polyolefin added with thermoplastic materials.

* * * * *

UNITED STATES PATENT AND TRADEMARK OFFICE
CERTIFICATE OF CORRECTION

PATENT NO. : 12,145,301 B2
APPLICATION NO. : 17/861541
DATED : November 19, 2024
INVENTOR(S) : Guido Bonelli It is certified that error appears in the above-identified patent and that said Letters Patent is hereby corrected as shown below:

On the Title Page

(71) Applicant address information should be listed as:
- Fameccanica.Data S.p.A., San Giovanni Teatino (Chieti), ITALY -

(72) Inventor address information should be listed as:
- Guido BONELLI, San Giovanni Teatino (Chieti), ITALY -

Signed and Sealed this
Twenty-fifth Day of March, 2025

Coke Morgan Stewart
*Acting Director of the United States Patent and Trademark Office*